United States Patent
Bolton

(10) Patent No.: US 10,661,243 B2
(45) Date of Patent: May 26, 2020

(54) PROCESS AND APPARATUS FOR ETHANOL DEHYDRATION

(71) Applicant: Technip E&C Limited, Milton Keynes (GB)

(72) Inventor: Leslie William Bolton, Middlesex (GB)

(73) Assignee: Technip E&C Limited, Milton Keynes (GB)

( * ) Notice: Subject to any disclaimer, the term of this patent is extended or adjusted under 35 U.S.C. 154(b) by 0 days.

(21) Appl. No.: 15/538,777

(22) PCT Filed: Dec. 8, 2015

(86) PCT No.: PCT/EP2015/079030
§ 371 (c)(1),
(2) Date: Jun. 22, 2017

(87) PCT Pub. No.: WO2016/096544
PCT Pub. Date: Jun. 23, 2016

(65) Prior Publication Data
US 2017/0368522 A1     Dec. 28, 2017

(30) Foreign Application Priority Data
Dec. 16, 2014  (EP) ..................................... 14198385

(51) Int. Cl.
*C07C 1/24* (2006.01)
*B01J 8/04* (2006.01)
*C07C 11/04* (2006.01)

(52) U.S. Cl.
CPC ............... *B01J 8/0496* (2013.01); *C07C 1/24* (2013.01); *C07C 11/04* (2013.01); *B01J 2208/00176* (2013.01); *B01J 2208/00539* (2013.01)

(58) Field of Classification Search
None
See application file for complete search history.

(56) References Cited

U.S. PATENT DOCUMENTS

| 3,969,196 A | 7/1976 | Zosel |
| 4,123,448 A | 10/1978 | Kleinpeter |

(Continued)

FOREIGN PATENT DOCUMENTS

| EP | 1925363 | 5/2008 |
| EP | 1982761 | 10/2008 |

(Continued)

OTHER PUBLICATIONS

Chang et al., "A Lumped Kinetic Model for Dehydration of Ethanol to Hydrocarbons Over HZSM-5," Chem. Eng Comm. 1990, 95: pp. 27 to 39.

(Continued)

*Primary Examiner* — Philip Y Louie
(74) *Attorney, Agent, or Firm* — Arnall Golden Gregory LLP

(57) ABSTRACT

The present invention provides a process for the preparation of ethene by vapour phase chemical dehydration of ethanol using an adiabatic reactor, wherein the interior of the adiabatic reactor is separated into at least three reaction zones, comprising a first reaction zone, at least one intermediate reaction zone and a final reaction zone, and wherein each zone contains an ethanol dehydration catalyst; said process comprising the steps of; a) feeding a pre-heated reactant feed-stream into an inlet of the first reaction zone; b) extracting an effluent-stream from an outlet of the first reaction zone; c) feeding said effluent-stream into an inlet of a subsequent intermediate reaction zone; d) extracting an effluent-stream from an outlet of the intermediate reaction zone; e) repeating steps (c) and (d) for any subsequent intermediate reaction zones, if present; f) feeding, into an inlet of the final reaction zone, the effluent-stream from the preceding intermediate reaction zone; g) extracting a product stream from an outlet of the final reaction zone; wherein (Continued)

the effluent-streams are re-heated prior to being fed into a subsequent reaction zone by means of one or more heat exchangers and; and wherein a single heat exchanger simultaneously re-heats at least two of the effluent-streams, such that no more than one heat exchanger is present for every two effluent-streams being re-heated in the process.

14 Claims, 3 Drawing Sheets

(56) References Cited

U.S. PATENT DOCUMENTS

| | | | |
|---|---|---|---|
| 4,232,179 A | | 11/1980 | Valladares Barrocas et al. |
| 4,396,789 A | | 8/1983 | Barrocas et al. |
| 5,254,316 A | | 10/1993 | Zardi et al. |
| 2012/0310026 A1 | * | 12/2012 | Partington ................ C07C 1/20 585/639 |
| 2013/0178674 A1 | | 7/2013 | Taheri et al. |
| 2015/0352510 A1 | * | 12/2015 | Rizzi ...................... B01J 8/0469 422/310 |

FOREIGN PATENT DOCUMENTS

| | | | | |
|---|---|---|---|---|
| EP | 2759338 A1 | | 7/2014 | |
| GB | 516360 A | * | 1/1940 | ............... C07C 1/24 |
| JP | S5436203 A | | 3/1979 | |
| JP | S54010539 B1 | | 5/1979 | |
| JP | S5838220 A | | 3/1983 | |
| WO | WO-2007/063279 | | 6/2007 | |
| WO | WO-2007/063280 | | 6/2007 | |
| WO | WO-2007/063281 | | 6/2007 | |
| WO | WO-2007/063282 | | 6/2007 | |
| WO | WO-2007/134415 | | 11/2007 | |
| WO | WO-2008/062157 | | 5/2008 | |

OTHER PUBLICATIONS

Yue et al., "Kinetic Analysis of the Catalytic Dehydration of Alcohols Over Zeolites," Chem. Eng. Res. and Design 1984, 62: pp. 81 to 91.

International Search Report and Written Opinion for International Application No. PCT/EP2015/079030, dated May 18, 2016.

* cited by examiner

PROCESS AND APPARATUS FOR ETHANOL DEHYDRATION

The present invention relates to a process and apparatus for producing ethene by the vapour phase chemical dehydration of ethanol. In particular, the process of the invention includes use of an adiabatic reactor comprising multiple reaction zones in combination with an effluent-stream re-heating system where two or more different intermediate effluent-streams are re-heated by means of a single heat exchanger, without compromising the efficacy of the ethanol dehydration process.

Ethene is an important commodity chemical and monomer which has traditionally been produced industrially by the steam or catalytic cracking of hydrocarbons derived from crude oil. However, as reserves of crude oil diminish and prices rise there becomes an increasing need to find alternative economically viable methods of making this product. By virtue of its ready availability from the fermentation of biomass and synthesis gas based technologies, ethanol is emerging as an important potential feedstock from which ethene can be made in the future.

The dehydration of ethanol to ethene is a well-known reaction, and has been used in various commercial processes since the 1930s. The reaction is highly endothermic and as such requires high temperatures to achieve efficient conversion of ethanol to ethene. Early systems used isothermal reactors to achieve this goal, though were largely replaced by adiabatic reactor systems in the 1970s.

In a typical dehydration process, a feed comprising ethanol, optionally water and other components is continuously fed to a reactor containing a bed of heteropolyacid catalyst and the products continuously removed. Under steady state conditions, the feed entering the reactor is rapidly converted near the inlet into an equilibrium mixture of water, ethanol and ethoxyethane (the product of a rapid first stage dehydration of the ethanol). Such processes are typically conducted at elevated temperature and pressure.

Ethanol dehydration can be advantageously carried out using multiple adiabatic reactors arranged in series, with intermediate heating between reactors. Such systems typically include several individual pressure vessels wherein the effluent-streams from each reactor are each heated by a heat source prior to being fed into a subsequent reactor.

U.S. Pat. No. 4,232,179 discloses a process for dehydrating ethanol in which several adiabatic reactors are arranged in series. A heat carrying fluid is introduced into each reactor and mixed in with the reactor feed in order to maintain the required high temperature inside each reactor. The separated reactors of this process allow for the operation of a reactor, or series of reactors, to be interrupted for maintenance services without interfering with the performance of other reactors in the system, and thereby permitting process continuity.

US 2013/0178674 describes a process for the dehydration of ethanol using a reactor comprising a plurality of stages within a single reactor, wherein each stage has a different length, internal diameter, volume and quantity of catalyst. The heating of the feed to each stage is individually controlled by means of multiple heat exchangers, thereby allowing optimization of the temperature profile of each individual stage. Additionally, the reaction zones are each designed to operate under different conditions of temperature and pressure, reactant residence time, and quantity of catalyst, in order to obtain the highest efficiency for ethanol conversion, ethene selectivity, and yield. A further benefit of this design, as for U.S. Pat. No. 4,232,179, is that the separated character of each stage allows individual stages to be shut down for maintenance without interruption of the whole process.

However, a notable disadvantage of the system disclosed in U.S. Pat. No. 4,232,179 is the complexity and the footprint associated with the apparatus used. For instance, in order to provide reaction zones operating under different process conditions, complex piping networks are required for effluent-streams which are subjected to different levels of re-heating, according to the particular process conditions implemented in subsequent reaction zones.

It has been unexpectedly found that, despite the preference for optimizing the temperature of each reactor or reaction zone individually according to the prior art, heat exchangers used to re-heat effluent-streams of reactors or reaction zones of an ethanol dehydration system can be usefully combined into single units to simplify the overall system. Surprisingly, it has been found that re-heating two or more different effluent-streams to substantially the same extent by means of a single heat exchanger does not compromise the efficacy of an ethanol dehydration process operated with multiple reaction zones and can reduce complexity and overall costs by the use of fewer pressure vessels and simplified piping arrangements. This is of particular significance when the number of reaction zones becomes large (e.g. more than 4), as the piping and instrument layout in the vicinity of these reactors becomes extremely complicated due to the number of connections and external items required.

The complicated layout and piping arrangement of multiple reactor systems with large numbers of reactors or reaction zones makes them excessively difficult and costly to set up and maintain, rendering the use of such systems overly expensive. In particular, connecting a large number of heat exchangers to a single reactor with multiple reaction zones is geometrically awkward, and therefore likely to be costly and logistically difficult to maintain. A particular benefit of the present invention is that it reduces the number of heat exchangers that need to be arranged around the reactor, allowing for more simple piping arrangements and improved maintenance access.

Thus, the present invention is directed to a process and apparatus which simplifies the piping and instrument layout in the vicinity of ethanol dehydration reactors by combining multiple reactors into a single pressure vessel comprising multiple reaction zones, and combining the reheating of two or more intermediate effluent-streams in a single external device. Reference herein to an "intermediate effluent-stream" or an "effluent-stream" is intended to refer to an effluent-stream from a reaction zone of the reactor which is re-heated before being conveyed to a subsequent reaction zone of the reactor for further processing.

In a first aspect, the present invention provides a process for the preparation of ethene by vapour phase chemical dehydration of ethanol using an adiabatic reactor, wherein the interior of the adiabatic reactor is separated into at least three reaction zones, comprising a first reaction zone, at least one intermediate reaction zone and a final reaction zone, and wherein each zone contains an ethanol dehydration catalyst; said process comprising the steps of;
  a) feeding a pre-heated reactant feed-stream into an inlet of the first reaction zone;
  b) extracting an effluent-stream from an outlet of the first reaction zone;
  c) feeding said effluent-stream into an inlet of a subsequent intermediate reaction zone;

d) extracting an effluent-stream from an outlet of the intermediate reaction zone;
e) repeating steps (c) and (d) for any subsequent intermediate reaction zones, if present;
f) feeding, into an inlet of the final reaction zone, the effluent-stream from the preceding intermediate reaction zone;
g) extracting a product stream from an outlet of the final reaction zone;

wherein the effluent-streams are re-heated prior to being fed into a subsequent reaction zone by means of one or more heat exchangers; and wherein a single heat exchanger simultaneously re-heats at least two of the effluent-streams, such that no more than one heat exchanger is present for every two effluent-streams being re-heated in the process.

The combination and re-use of elements of the process greatly simplifies the arrangement of multi-reactor systems, allowing for reduced costs compared to conventional processes. In particular, combining heat exchangers into single units allows multiple effluent-streams to be simultaneously reheated. This greatly reduces the number of heat exchangers that need to be arranged around the reactor, and therefore the complexity of the piping and instrument layout in the vicinity of the reactor, which otherwise becomes extremely complicated due to the number of connections and external items required when multiple reaction zones are present.

The reactor used in the process according to the present invention comprises at least three reaction zones; a first reaction zone, at least one intermediate reaction zone and a final reaction zone. The present invention is particularly effective where the number of intermediate reaction zones is three or more (for example, 4 or 5 intermediate reaction zones), when the piping and instrument layout around the reactor becomes increasingly complicated. The present invention is compatible with scaled-up ethanol dehydration systems having large reactors with increased numbers of reaction zones (for example, 4 or 5 intermediate reaction zones).

The heat exchangers of the present invention may be selected from any multi-stream heat exchangers commonly known in the art. Preferably, the heat exchangers used in the present invention are shell and tube heat exchangers or plate/frame heat exchangers. The heat exchangers may be single-phase or two-phase heat exchangers.

A shell and tube heat exchanger commonly comprises a large pressure vessel (shell), through which tubes or bundles of tubes pass. One fluid runs through the shell while a second fluid runs through the tubes, wherein said fluids are in thermal contact through the surface of the tubes. Heat is transferred between a fluid in the shell and a fluid in the tubes, via the tube walls.

A plate/frame heat exchanger commonly comprises a series of plate-like chambers, thin in depth, and thermally contacted on their largest surface. The "hot" and "cold" fluid streams pass through alternating plates in the series, facilitating efficient heat transfer between the fluids.

In one embodiment of the present invention, at least one of the one or more heat exchangers is a shell and tube type heat exchanger. Preferably, the shell and tube heat exchanger re-heats between two and four effluent-streams simultaneously, more preferably two effluent-streams simultaneously. Multiple effluent-streams may be simultaneously re-heated by passing separate effluent-streams through separate tubes or groups of tubes within a single shell.

In another embodiment of the present invention, at least one of the one or more heat exchangers is a plate/frame type heat exchanger. Preferably, the plate/frame type heat exchanger re-heats at least four effluent-streams simultaneously. Multiple effluent-streams may be simultaneously re-heated by passing separate effluent-streams through separate plates or series of plates within a single heat exchanger.

It is possible to provide heat exchangers which accommodate multiple effluent-streams for reheating, wherein the degree of heating of the multiple effluent-streams is substantially the same. This can be achieved by ensuring that the contact surface area between one effluent-stream and the heating element of the heat exchanger is as close as possible to that of further effluent-stream reheated in the same unit. In a preferred embodiment of the present invention, the difference in contact surface area between the two or more effluent-streams being re-heated in a single heat exchanger and respective heating elements of the heat exchanger is less than 10%, preferably less than 5%, more preferably less than 2%. In a more preferred embodiment of the present invention, the contact surface area between the two or more effluent-streams being re-heated in a single heat exchanger and the respective heating elements of the heat exchanger is identical.

The dehydration of the feedstock according to the present invention is believed (Chem. Eng Comm. 1990, 95, 27 to 39) to proceed by either the direct dehydration to olefin(s) and water (Equation 1); or via an ether intermediate (Equations 2 and 3).

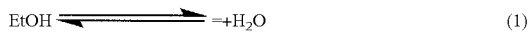  (1)

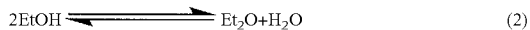  (2)

  (3)

The direct conversion of the ether to two moles of olefin and water has also been reported (Chem. Eng. Res. and Design 1984, 62, 81 to 91). All of the reactions shown above are typically catalysed by Lewis and/or Bronsted acids. Equation 1 shows the endothermic direct elimination of ethanol to ethene and water; competing with Equation 1 are Equations 2 and 3 i.e. the exothermic etherification reaction (Equation 2), and the endothermic elimination of ethoxyethane to produce ethene and ethanol (Equation 3). However, the dehydration reaction of ethanol to ethene is overall said to be highly endothermic.

The ethanol dehydration catalyst used in the process of the present invention can be selected from those commonly known in the art, such as a fixed bed dehydration catalyst. The catalyst is preferably a heteropolyacid catalyst selected from those described in WO2008062157, WO2007063282, WO2007063281, WO2007063280, WO2007063279, EP1925363 and EP1982761.

According to the present invention, there is provided a process for the preparation of ethene by vapour phase chemical dehydration of a feed-stream comprising ethanol (and preferably water and/or ethoxyethane), said process comprising contacting the feed-stream with a catalyst in multiple reaction zones of an adiabatic reactor, wherein the complexity of the piping and instrument layout in the vicinity of the reactor is greatly reduced.

Preferably, the amount of water in the feed-stream of the process of the present invention is at most about 50 wt. %, more preferably at most about 20 wt. %, most preferably at most about 10 wt. %, or even at most about 7 wt. %, based on the total weight of water, ethanol and ethoxyethane in the reactant feed-stream. Preferably, the amount of water in the reactant feed-stream is at least about 0.1 wt. %, more preferably at least about 0.5 wt. % and most preferably at least about 1 wt. %, based on the total weight of water, ethanol and ethoxyethane in the reactant feed-stream.

The liquid product stream following olefin removal comprises mostly unreacted ethanol, diethyl ether and water. The applicants have found that it is particularly preferable to recycle the major portion of the alcohols and ethers back to the vapour phase dehydration reactor after water by-product removal.

In some embodiments of the invention, the feed-stream comprises an inert diluent. In other embodiments, an inert diluent is added between reaction zones. Preferred diluents comprise nitrogen, helium, ethene and/or saturated hydrocarbons, for example hexanes, 2-methylpropane or n-butane. More preferably, the feed-stream diluent is selected from nitrogen and/or helium.

In one embodiment, the reaction zones in which the ethanol is dehydrated according to the present invention, are preferably operated at a temperature of from 160° C. to 270° C., more preferably from 180° C. to 270° C., more preferably from 190° C. to 260° C. and most preferably from 200° C. to 250° C. The reaction zones are preferably operated at a pressure of from 0.1 MPa to 4.5 MPa, preferably at a pressure of from 1.5 MPa to 3.5 MPa, and most preferably at a pressure of from 1.8 MPa to 2.8 MPa.

In another embodiment, the feed temperatures for the reaction zones in which the ethanol is dehydrated according to the present invention are preferably at least about 252° C., more preferably at least about 255° C., even more preferably at least about 260° C., even more preferably still at least about 280° C. and most preferably at least 300° C. The upper limit of the feed temperature is below the temperature at which selectivity for ethene is negatively impacted and/or one which is overly energy intensive. Preferably, the upper limit of the feed temperature is about 350° C., more preferably about 325° C. Thus, preferred feed temperature ranges for the dehydration reaction include: a) at least about 252° C. to about 350° C.; b) at least about 252° C. to about 325° C.; c) at least about 255° C. to about 350° C.; d) at least about 255° C. to about 325° C.; e) at least about 260° C. to about 350° C.; f) at least about 260° C. to about 325° C.; g) at least about 280° C. to about 350° C.; h) at least about 280° C. to about 325° C.; i) at least about 300° C. to about 350° C.; and j) at least about 300° C. to about 325° C. In this embodiment the reaction zones have an internal pressure of from about 0.90 MPa to about 1.60 MPa and more preferably, an internal pressure of from about 0.95 MPa to about 1.30 MPa. Most preferably, the reaction zones have an internal pressure of from about 1.00 MPa to about 1.20 MPa.

Reference to "feed temperature" herein is intended to refer to the temperature of a particular stream at the point at which it is fed to a reactor or reaction zone.

Reference herein to the pressure inside the reaction zones corresponds to the sum of the partial pressures of the reactants, namely those of ethanol and (if present) water and ethoxyethane, as well as the partial pressure of the ethylene product. Unless otherwise indicated herein, partial pressures of inert diluents, such as helium and nitrogen, or other inert components are excluded from the total stated pressure. Thus, reference to reaction zone pressure herein is in accordance with the formula: $P_{reactor} = P_{water} + P_{ethanol} + P_{ethoxyethane} + P_{ethylene}$. Furthermore, unless otherwise indicated, reference to reactor pressures herein is to absolute pressures, and not gauge pressures.

In a preferred embodiment of the process according to the present invention, the difference between the temperatures of the individual intermediate effluent-streams, after they are re-heated, is less than 20° C., more preferably less than 10° C. and most preferably less than 5° C. Preferably, the difference between the temperatures of the individual intermediate effluent-streams, before they are re-heated, is less than 20° C., more preferably less than 10° C. and most preferably less than 5° C.

Preferably, the difference in reaction pressures between different reaction zones in the process according to the present invention is less than 1 MPa, more preferably less than 0.5 MPa, and most preferably less than 0.3 MPa.

The GHSV for continuous operation of the reactor for ethanol dehydration in accordance with the present invention may suitably be in the range 50 to 50,000 $h^{-1}$, preferably from 1,000 to 30,000 $h^{-1}$, more preferably from 2,000 to 15,000 $h^{-1}$ and most preferably from 5,000 to 8,000 $h^{-1}$. 'Gas hourly space velocity'(GHSV) is defined as the volume of gas fed per unit volume of catalyst per hour, at standard temperature (0° C.) and pressure (0.101325 MPa).

The present invention additionally provides an apparatus for preparing ethene by vapour phase chemical dehydration of ethanol, comprising;
  i) an adiabatic reactor, wherein the interior of the adiabatic reactor is separated into at least three reaction zones, comprising a first reaction zone, at least one intermediate reaction zone and a final reaction zone;
  ii) a means for feeding a pre-heated reactant stream into an inlet of the first reaction zone;
  iii) a means for extracting an effluent-stream from an outlet of the first reaction zone;
  iv) a means for feeding said effluent-stream into an inlet of a subsequent intermediate reaction zone;
  v) a means for extracting an effluent-stream from an outlet of the intermediate reaction zone;
  vi) one or more means for feeding to, and one or more means for extracting an effluent-stream from, any additional intermediate reaction zones if present;
  vii) a means for feeding, into an inlet of the final reaction zone, the effluent-stream from the preceding intermediate reaction zone;
  viii) a means for extracting a product stream from an outlet of the final reaction zone;
  ix) one or more heat exchangers for re-heating each effluent-stream, prior to being fed into a subsequent reaction zone, wherein a single heat exchanger is configured to simultaneously re-heat at least two of the effluent-streams, such that no more than one heat exchanger is present for every two effluent-streams being re-heated.

The reactor according to the apparatus of the present invention comprises at least three reaction zones; a first reaction zone, at least one intermediate reaction zone and a final reaction zone. The present invention is particularly effective in the case that the number of intermediate reaction zones is three or more, when the piping and instrument layout around the reactor becomes increasingly complicated.

The adiabatic reactor according to the apparatus of the present invention may comprise a single pressure vessel, wherein the interior of the reactor is divided into three or more reaction zones. The means for dividing the interior of the reactor may comprise a simple baffle, wherein the reactor is configured to allow a difference in reaction pressures between different reaction zones of less than 1 MPa, more preferably less than 0.5 MPa, and most preferably less than 0.3 MPa.

The reaction zones of the adiabatic reactor according to the present invention may each individually have the interior function of an adiabatic reactor such as those known commonly in the art, for example a fixed bed tubular reactor or radial flow reactor.

A simple fixed bed tubular reactor comprises a tubular passage filled with a fixed bed of catalyst through which a feed is passed. A fixed bed radial flow reactor comprises a reactor configured such that a feed flows radially outward through fixed annular beds of catalyst.

The heat exchangers of the apparatus according to the present invention may be selected from any multi-stream heat exchangers commonly known in the art. Preferably, the heat exchangers used in the present invention are shell and tube heat exchangers or plate/frame heat exchangers. The heat exchangers may be single-phase or two-phase heat exchangers.

In one embodiment of the present invention, wherein at least one of the one or more heat exchangers is a shell and tube heat exchanger, the apparatus is configured such that each shell and tube heat exchanger re-heats between two and four effluent-streams simultaneously, preferably two effluent-streams simultaneously.

In another embodiment of the present invention, wherein at least one of the one or more heat exchangers is a plate/frame heat exchanger, the apparatus is configured such that each plate/frame heat exchanger re-heats at least two effluent-streams simultaneously, preferably at least four effluent-streams simultaneously.

The heat exchangers according to a preferred embodiment of the apparatus of the present invention may be configured such that the difference in contact surface area between the two or more effluent-streams being re-heated in a single heat exchanger and respective heating elements of the heat exchanger is less than 10%, preferably less than 5%, more preferably less than 2%.

In a different embodiment, the contact surface area between the two or more effluent-streams being re-heated in a single heat exchanger and the respective heating elements of the heat exchanger is configured to be identical.

The invention will now be described in greater detail with reference to the embodiments of the invention illustrated in the accompanying figures, in which.

Figure 1:
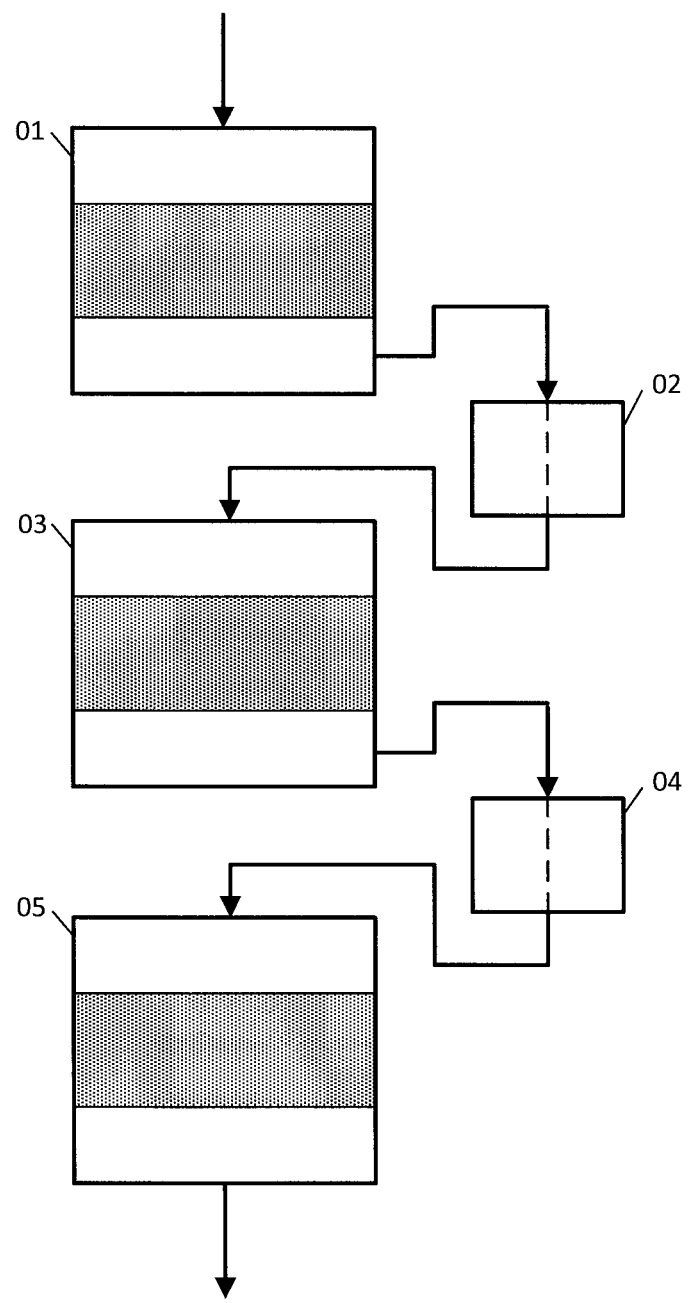
FIG. 1 shows a conventional system comprising multiple reactors in series (01, 03, 05) with multiple re-heating means (02, 04), such as heat exchangers, wherein the effluent-stream from each reactor is individually heated prior to being fed into a subsequent reactor.
Figure 2:
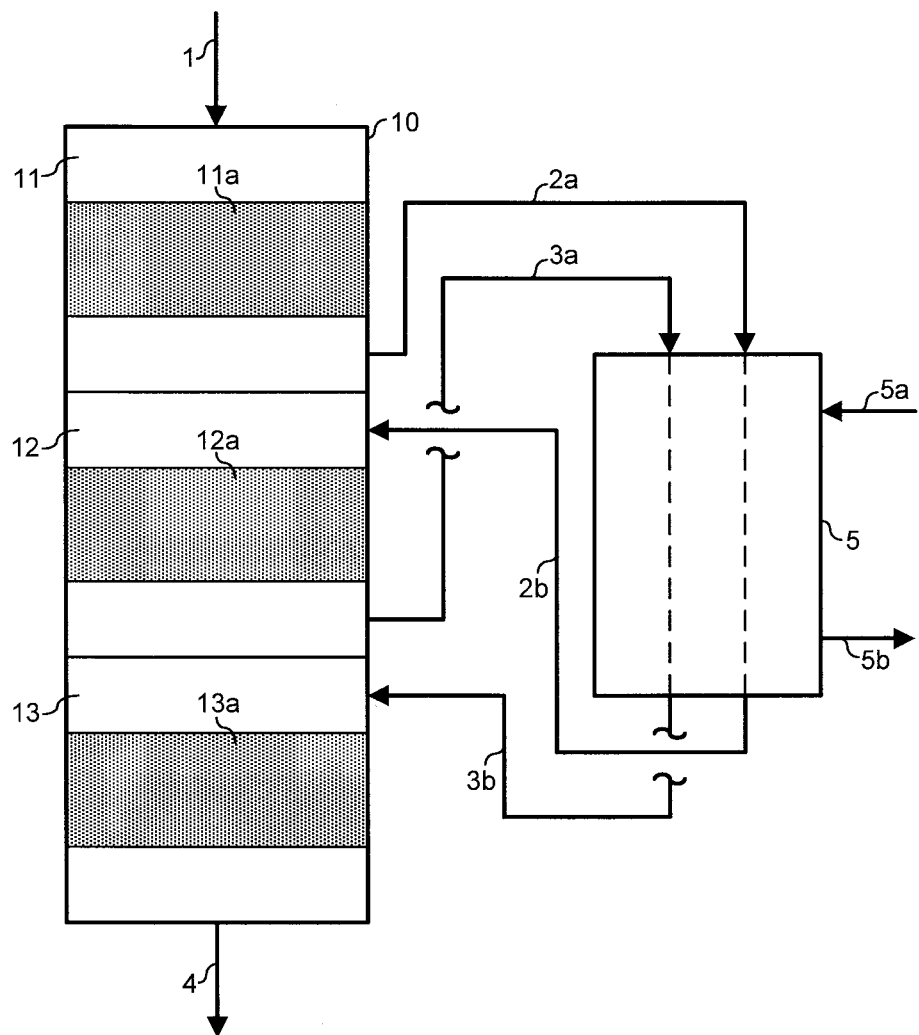
FIG. 2 shows a simplified reactor system comprising three reaction zones in series, sharing a single heat exchanger for re-heating two streams, in accordance with the present invention.

The embodiment of the present invention shown in FIG. 2 demonstrates a simplified reactor system compared to the equivalent conventional multiple reactor and heat exchanger system shown in FIG. 1. Specifically, in the embodiment of the invention according to FIG. 2, an adiabatic reactor (10) is internally separated into a first reaction zone (11), an intermediate reaction zone (12), and a final reaction zone (13), each containing a fixed bed dehydration catalyst (11a, 12a, and 13a respectively).

A pre-heated reactant stream (1) is fed into an inlet of the first reaction zone (11) and comes into contact with the first dehydration catalyst (11a). An effluent-stream (2a) is extracted from an outlet of the first reaction zone (11) and fed into a heat exchanger (5), wherein the effluent-stream (2a) is re-heated by heat exchange with a heat carrying stream (5a). The re-heated stream (2b) is fed into an inlet of the intermediate reaction zone (12), wherein it comes into contact with the intermediate dehydration catalyst (12a). An effluent-stream (3a) is extracted from an outlet of the intermediate reaction zone (12) and fed into the same aforementioned heat exchanger (5), wherein the effluent-stream (3a) is re-heated by heat exchange with heat carrying stream (5a). The reheated stream (3b) is fed into an inlet of the final reaction zone (13), wherein it comes into contact with the final dehydration catalyst (13a). An effluent product stream (4) is then extracted from an outlet of the final reaction zone (13).

Figure 3:
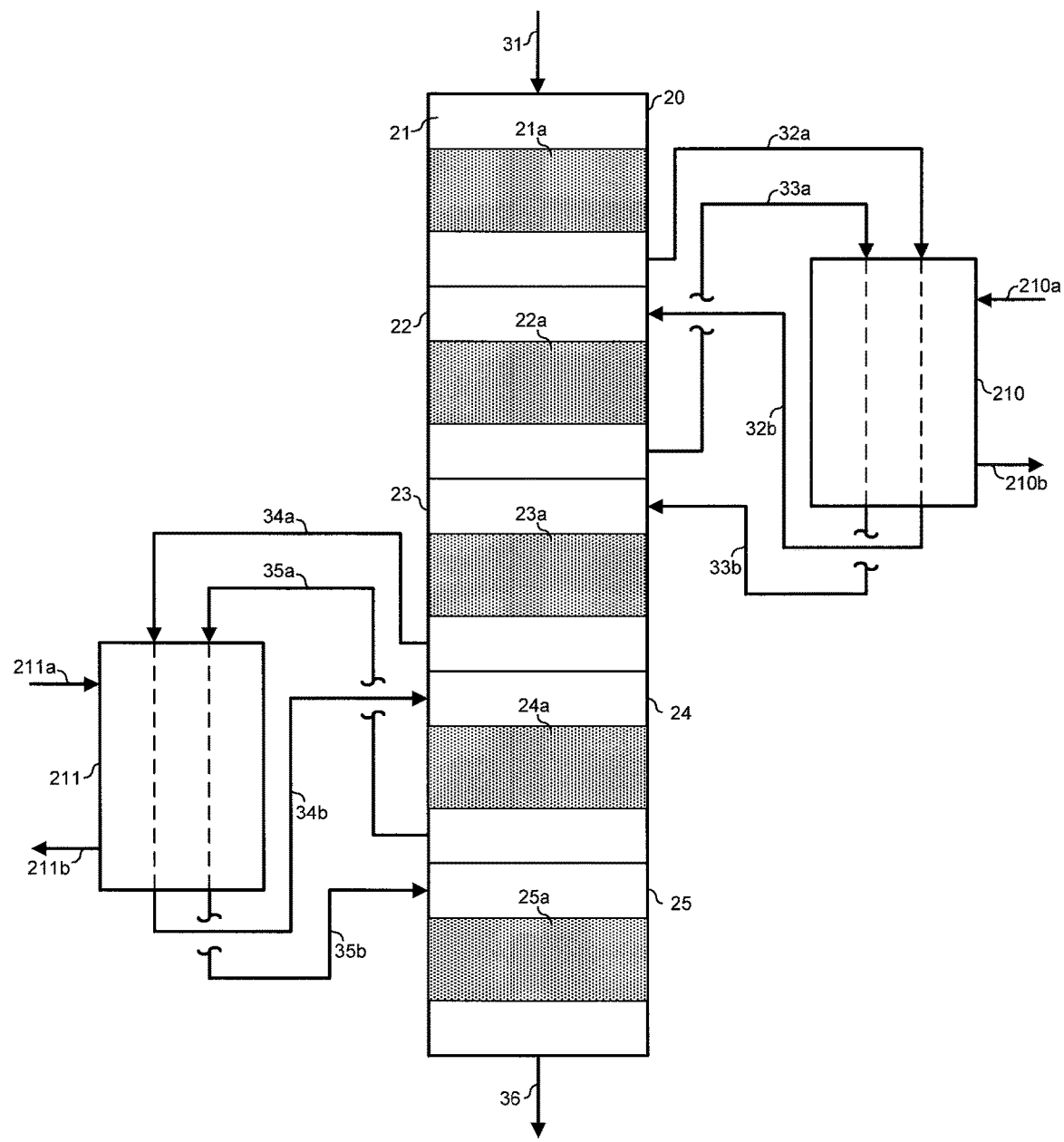
FIG. 3 shows a different embodiment of a simplified reactor system comprising five reaction zones in series, with two heat exchangers re-heating two streams each, in accordance with the present invention.

The invention is also particularly effective for simplifying the arrangement of larger reactor systems. This is demonstrated in the embodiment of the invention shown in FIG. 3, wherein an adiabatic reactor (20) is internally separated into a first reaction zone (21), three intermediate reaction zones (22, 23, and 24), and a final reaction zone (25), each containing a fixed bed dehydration catalyst (21a, 22a, 23a, 24a, and 25a respectively).

A pre-heated reactant stream (31) is fed into an inlet of the first reaction zone (21) and comes into contact with a dehydration catalyst (21a). An effluent-stream (32a) is extracted from an outlet of the first reaction zone (21) and fed into a first heat exchanger (210), wherein the effluent-stream (32a) is re-heated by heat exchange with a heat carrying stream (210a). The re-heated stream (32b) is fed into an inlet of the first intermediate reaction zone (22), wherein it comes into contact with a dehydration catalyst (22a). An effluent-stream (33a) is extracted from an outlet of the first intermediate reaction zone (22) and fed into the same aforementioned first heat exchanger (210), wherein the effluent-stream (33a) is re-heated by heat exchange with heat carrying stream (210a).

The reheated stream (33b) is fed into an inlet of the second intermediate reaction zone (23), wherein it comes into contact with a dehydration catalyst (23a). An effluent-stream (34a) is extracted from an outlet of the second intermediate reaction zone (23) and fed into a second heat exchanger (211), wherein the effluent-stream (34a) is re-heated by heat exchange with heat carrying stream (211a). The reheated stream (34b) is fed into an inlet of the third intermediate reaction zone (24), wherein it comes into contact with a dehydration catalyst (24a). An effluent-stream (35a) is extracted from an outlet of the third intermediate reaction zone (24) and fed into the same aforementioned second heat exchanger (211), wherein the effluent-stream (35a) is re-heated by heat exchange with heat carrying stream (211a). The reheated stream (35b) is fed into an inlet of the final reaction zone (25), wherein it comes into contact with the final dehydration catalyst (25a). An effluent product stream (36) is then extracted from an outlet of the final reaction zone (25).

A conventional system comprising five reactors would require four heat exchangers between the reactors in order to re-heat intermediate streams. The layout and piping arrangement of such a large system would be geometrically awkward and costly to set up and maintain, potentially rendering the use of a system of this size and complexity not economically viable. The present invention provides a means for reducing the number of pressure vessels required for a reactor system, which simplifies the layout of the system and reduces the difficulty and cost of construction and maintenance operations.

The invention claimed is:

1. A process for the preparation of ethene by vapour phase chemical dehydration of ethanol using an adiabatic reactor, wherein the interior of the adiabatic reactor is separated into at least three reaction zones, comprising a first reaction zone, at least one intermediate reaction zone and a final reaction zone, wherein the reaction zones are operated at a temperature of from 160° C. to 270° C., and wherein each zone contains an ethanol dehydration catalyst; said process comprising the steps of;
   a) feeding a pre-heated reactant feed-stream comprising ethanol into an inlet of the first reaction zone;
   b) extracting an effluent-stream from an outlet of the first reaction zone;
   c) feeding said effluent-stream into an inlet of a subsequent intermediate reaction zone;
   d) extracting an effluent-stream from an outlet of the intermediate reaction zone;
   e) repeating steps (c) and (d) for any subsequent intermediate reaction zones, if present;
   f) feeding, into an inlet of the final reaction zone, the effluent-stream from the preceding intermediate reaction zone;
   g) extracting a product stream comprising ethene from an outlet of the final reaction zone;
      wherein the effluent-streams are re-heated prior to being fed into a subsequent reaction zone by means of one or more heat exchangers; and
      wherein a single heat exchanger simultaneously re-heats at least two of the effluent-streams, such that no more than one heat exchanger is present for every two effluent-streams being re-heated in the process.

2. The process of claim 1, wherein a single heat exchanger re-heats between two and four effluent-streams simultaneously.

3. The process of claim 1, wherein a single heat exchanger re-heats two streams simultaneously.

4. The process of claim 1, wherein there are more than two intermediate reaction zones.

5. The process of claim 1, wherein the heat exchanger(s) is/are selected from shell and tube heat exchangers and/or plate/frame heat exchangers.

6. The process of claim 1, wherein a difference in contact surface area between the at least two effluent-streams being re-heated in a single heat exchanger and respective heating elements of the heat exchanger is less than 10%.

7. The process of claim 1, wherein a contact surface area between the two or more effluent-streams being re-heated in a single heat exchanger and respective heating element of the heat exchanger is identical.

8. The process of claim 1, wherein a difference in pressure between individual reaction zones is less than 1 MPa.

9. The process of claim 1, wherein a difference between temperatures of individual intermediate effluent-streams, after they are re-heated, is less than 20° C.

10. The process of claim 1, wherein a difference between temperatures of individual intermediate effluent-streams, before they are re-heated, is less than 20° C.

11. The process of any one of claim 1, wherein there are between three and five intermediate reaction zones.

12. The process of claim 1, wherein a difference in contact surface area between the at least two effluent-streams being re-heated in a single heat exchanger and respective heating elements of the heat exchanger is less than 2%.

13. The process of claim 1, wherein a difference in pressure between individual reaction zones is less than 0.3 MPa.

14. The process of claim 1, wherein a difference between temperatures of the individual intermediate effluent-streams, before or after they are re-heated, is less than 5° C.

* * * * *